United States Patent
Li et al.

(10) Patent No.: US 11,180,449 B2
(45) Date of Patent: Nov. 23, 2021

(54) CRYSTAL FORM OF KEY INTERMEDIATE OF BRUTON TYROSINE KINASE (BTK) INHIBITOR AND PREPARATION METHOD THEREOF

(71) Applicant: SHANGHAI ZAIQI BIO-TECH CO., LTD., Shanghai (CN)

(72) Inventors: Chao Li, Shanghai (CN); Peng Sun, Shanghai (CN); Beibei Tian, Shanghai (CN); Xin Zhang, Shanghai (CN)

(73) Assignee: SHANGHAI ZAIQI BIO-TECH CO., LTD., Shanghai (CN)

( * ) Notice: Subject to any disclaimer, the term of this patent is extended or adjusted under 35 U.S.C. 154(b) by 0 days.

(21) Appl. No.: 17/341,420

(22) Filed: Jun. 8, 2021

(65) Prior Publication Data

US 2021/0300866 A1    Sep. 30, 2021

Related U.S. Application Data

(63) Continuation of application No. PCT/CN2020/100245, filed on Jul. 3, 2020.

(30) Foreign Application Priority Data

Jul. 9, 2019 (CN) .......................... 201910614068.1

(51) Int. Cl.
*C07D 207/34*    (2006.01)

(52) U.S. Cl.
CPC ........ *C07D 207/34* (2013.01); *C07B 2200/13* (2013.01)

(58) Field of Classification Search
CPC .................................................. C07D 207/34
See application file for complete search history.

(56) References Cited

U.S. PATENT DOCUMENTS

| 8,063,241 | B2 | 11/2011 | Lorenz et al. |
| 8,816,125 | B2 | 8/2014 | Michalczak et al. |
| 10,040,753 | B2 | 8/2018 | Lehner et al. |

FOREIGN PATENT DOCUMENTS

| CN | 106573001 A | 4/2017 |
| CN | 108570036 A | 9/2018 |
| CN | 110372562 A | 10/2019 |
| WO | 2017118277 A1 | 7/2017 |
| WO | 2018210296 A1 | 11/2018 |

OTHER PUBLICATIONS

B. Rodriguez-Spong et al. (Advanced Drug Delivery Reviews, 2004, 56, p. 263).*
Yu Wang et al., 11.3 Study on drug morphology, Thermal analysis and drug analysis, Jun. 1, 2015, pp. 96-98, Beijing Medical Science and Technology Press, Beijing, China.
Desen Su et al., Section 5 Preparation of drug polymorphs, Physical Pharmacy, Jul. 1, 2004, pp. 17-18, Chemical Industry Press, Beijing, China.
Internation Search Report of PCT/CN2020/100245, dated Sep. 30, 2020.

* cited by examiner

*Primary Examiner* — Valerie Rodriguez-Garcia
(74) *Attorney, Agent, or Firm* — True Shepherd LLC; Andrew C. Cheng

(57) ABSTRACT

The present disclosure relates to a crystal form of a key intermediate of a bruton tyrosine kinase (BTK) inhibitor and a method for preparing the crystal form, and belongs to the technical field of medicine. The crystal form is a crystal form II of (R)-1-(1-(tert-butyloxyl)pyrrolidine-3-yl)-3-cyano-4-(4-(2,6-difluorophenoxyl)phenyl)-1H-pyrrole-2-ethyl formate. The obtained crystal form II of (R)-1-(1-(tert-butyloxyl)pyrrolidine-3-yl)-3-cyano-4-(4-(2,6-difluorophenoxyl)phenyl)-1H-pyrrole-2-ethyl formate has good chemical stability and crystal form stability and is convenient for storage and transportation. Meanwhile, the intermediate can be highly purified and a sample with a purity of 99.7% is obtained. The crystal form is important for quality control of a BTK inhibitor (R)-4-amino-1-(1-(butyl-2-alkynyl)pyrrolidine-3-yl)-3-(4-(2,6-difluorophenoxyl)phen yl)-1,6-dihydro-7H-pyrrolo[2,3-d]pyridazin-7-one, has a simple preparation process and is suitable for industrial production.

6 Claims, 7 Drawing Sheets

CRYSTAL FORM OF KEY INTERMEDIATE OF BRUTON TYROSINE KINASE (BTK) INHIBITOR AND PREPARATION METHOD THEREOF

CROSS-REFERENCE TO RELATED APPLICATIONS

This application is a continuation of International Patent Application No. PCT/CN2020/100245 with a filing date of Jul. 3, 2020, designating the United States, now pending, and further claims priority to Chinese Patent Application No. 201910614068.1 with a filing date of Jul. 9, 2019. The content of the aforementioned applications, including any intervening amendments thereto, are incorporated herein by reference.

TECHNICAL FIELD

The present disclosure relates to a crystal form of a key intermediate of a bruton tyrosine kinase (BTK) inhibitor and a method for preparing the crystal form, particularly relates to a crystal form II of (R)-1-(1-(tert-butyloxyl)pyrrolidine-3-yl)-3-cyano-4-(4-(2,6-difluorophenoxyl)phenyl)-1H-pyrrole-2-ethyl formate and a method for preparing the crystal form II and belongs to the technical field of medicine.

BACKGROUND

Immune cells can be broadly divided into two categories: T cells and B cells. The B cells function primarily by secreting antibodies to help body resist foreign invasions. Bruton tyrosine kinase (BTK) is a member of a tyrosine kinase subfamily, belongs to a Tec family of kinases, and is mainly expressed in hematopoietic cells and distributed in lymphatic, hematopoietic and blood systems. The BTK is a key kinase in a BCR signaling pathway, can regulate maturation and differentiation of normal B cells, and is also closely related to B-cell lymphoid tissue disorders. Therefore, targeting the small molecule inhibitor BTK provides benefits for treating B cell malignancies and autoimmune diseases.

Ibrutinib is a first-generation small molecule BTK inhibitor jointly developed by Pharmacyclics and Janssen. It was first approved by the FDA for treating mantle cell lymphoma (MCL) in November 2013, and subsequently approved for treating chronic lymphocytic leukemia (CLL) in February 2014. The ibrutinib can irreversibly bind to Cys481 in an ATP binding region of the BTK through its Michael receptor, resulting in inhibiting transmission of downstream signals by the BTK and effectively controlling growth of tumor cells. The ibrutinib transfers signals in a BCR signaling pathway and a cytokine receptorsignaling pathway and mediates migration, chemotaxis and adhesion of B cells. Preclinical studies have proved that the ibrutinib can inhibit proliferation and survival of malignant B cells.

PCT/US2014/061393 relates to a compound of a formula II (a structural formula is as follows), namely (R)-4-amino-1-(1-(butyl-2-alkynyl)pyrrolidine-3-yl)-3-(4-(2,6-difluorophenoxyl)phen yl)-1,6-dihydro-7H-pyrrolo[2,3-d]pyridazin-7-one. The compound is a new type of a BTK inhibitor and improves kinase selectivity, clinical efficacy or indications, and safety.

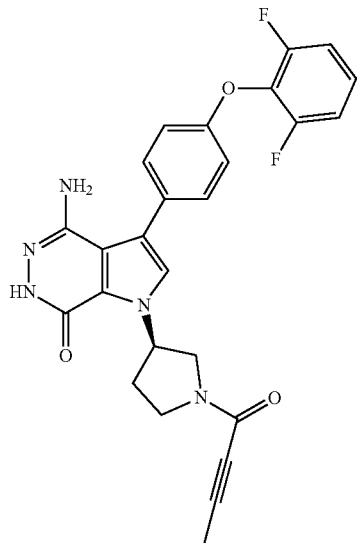

Formula II

It is reported that a purification of the (R)-4-amino-1-(1-(butyl-2-alkynyl)pyrrolidine-3-yl)-3-(4-(2,6-difluorophenoxyl)phen yl)-1,6-dihydro-7H-pyrrolo[2,3-d]pyridazin-7-one is achieved by silica gel column chromatography followed by crystallization, so that scaling-up of the purification of the BTK inhibitor is difficult and a large-scale production is not facilitated. As a human medicine, impurities in the BTK inhibitor often have an adverse effect on human body. Therefore, high-purity medicines are an important goal of medicine development. However, high-purity intermediates are essential to obtain the high-purity medicines.

As a key intermediate of the above-mentioned BTK inhibitor (R)-4-amino-1-(1-(butyl-2-alkynyl)pyrrolidine-3-yl)-3-(4-(2,6-difluorophenoxyl)phen yl)-1,6-dihydro-7H-pyrrolo[2,3-d]pyridazin-7-one, a (R)-1-(1-(tert-butyloxyl)pyrrolidine-3-yl)-3-cyano-4-(4-(2,6-difluorophenoxyl)phenyl)-1H-pyrrole-2-ethyl formate has high cost and low efficiency of purification by column chromatography, which is not conducive to industrial production. Therefore, it is urgent to develop a chemically stable intermediate that can be purified by crystallization, so that the purification of the new type of the BTK inhibitor (R)-4-amino-1-(1-(butyl-2-alkynyl)pyrrolidine-3-yl)-3-(4-(2,6-difluorophenoxyl)phen yl)-1,6-dihydro-7H-pyrrolo[2,3-d]pyridazin-7-one becomes easier. At the same time, an in-depth research is also necessary to find a new crystal form with higher crystal purity and good chemical stability.

SUMMARY

In order to solve the above technical problem, the present disclosure provides a crystal form II of (R)-1-(1-(tert-butyloxyl)pyrrolidine-3-yl)-3-cyano-4-(4-(2,6-difluorophenoxyl)phenyl)-1H-pyrrole-2-ethyl formate as shown in formula I and a method for preparing the crystal form. The crystal form has good stability.

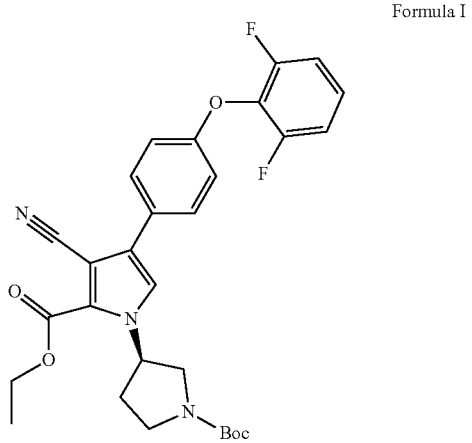 [SMILES: CCOC(=O)c1c(C#N)c(-c2ccc(Oc3c(F)cccc3F)cc2)cn1[C@@H]1CCN(C(=O)OC(C)(C)C)C1]

Formula I

Studies find that crystal products of a compound of formula I are obtained under different crystallization conditions and tested by X-ray diffraction (XRD) and differential scanning calorimetry (DSC). It is found that under the crystallization conditions, the same crystal form with good stability is obtained and named a crystal form II. A DSC pattern of the crystal form II shows a melting endothermic peak near 98° C. A Cu-Ka radiation is used to obtain an X-ray powder diffraction pattern expressed in 2θ angles and interplanar spacing. The X-ray powder diffraction pattern has the following characteristic peaks at 2θ: 9.34, 14.36, 18.79 and 19.02.

Further, in a specific example, an XRD pattern of the crystal form II of the (R)-1-(1-(tert-butyloxyl)pyrrolidine-3-yl)-3-cyano-4-(4-(2,6-difluorophenoxyl)phenyl)-1H-pyrrole-2-ethyl formate may have the following characteristic peaks at 2θ: 9.34, 11.85, 14.36, 14.52, 15.25, 17.16, 18.79, 19.02, 20.49, 20.79, 22.44 and 24.02.

Furthermore, in a specific example, an XRD pattern of the crystal form II of (R)-1-(1-(tert-butyloxyl)pyrrolidine-3-yl)-3-cyano-4-(4-(2,6-difluorophenoxyl)phenyl)-1H-pyrrole-2-ethyl formate may have the following characteristic peaks at 2θ: 5.52, 8.62, 9.34, 11.85, 14.36, 14.52, 15.25, 17.16, 18.79, 19.02, 20.02, 20.18, 20.49, 20.79, 22.44, 23.79, 24.02, 24.29 and 28.18.

In preparation processes in example 2-4, a typical pattern of the crystal form II of (R)-1-(1-(tert-butyloxyl)pyrrolidine-3-yl)-3-cyano-4-(4-(2,6-difluorophenoxyl)phenyl)-1H-pyrrole-2-ethyl formate is shown as FIG. 6.

Further, in the above technical scheme, a DSC curve of the crystal form II has an endothermic peak at 95° C.-105° C. Specifically, grinding and tableting are used. Obtained crystal forms are all determined to be a crystal form II. Positions of DSC absorption peaks are 100.10° C. and 101.20° C., respectively.

Term definition: "include" or "comprise" is an open-ended expression, that is, comprises the content specified in the present disclosure, does not exclude the content of other aspects.

"Crystal form" is used to describe an existence state of a solid compound and describes an aggregate of multiple parameters, composition of ions, atoms or molecules, symmetry properties and periodic arrangement, in crystals.

"Relative intensity" refers to a ratio of an intensity of a first strong peak to that of other peaks when the intensity of the first strong peak in a group of diffraction peaks attributed to a certain crystal form is defined as 100%.

In the context of the present disclosure, 2θ (also called 2theta or diffraction peak) values in an X-ray powder diffraction pattern are all in degrees (°).

When referring to a pattern and/or data in the pattern, a "diffraction peak" refers to a characteristic peak that is not attributed to background noise by those skilled in the art.

A measurement of 2θ or diffraction peaks of an X-ray powder diffraction pattern of an X-ray powder diffraction peak of the crystal form has experimental errors between different instruments and different samples.

The measurement of 2θ or diffraction peaks of an X-ray powder diffraction pattern may be slightly different. Experimental errors or differences may be +/−0.2 units or +/−0.1 units or +/−0.05 units, so that values of the 2θ or the diffraction peaks cannot be regarded as absolute.

A differential scanning calorimetric (DSC) curve of the crystal form has experimental errors between different instruments and different samples. Positions and peak values of an endothermic peak may be slightly different. Experimental errors or difference values may be less than or equal to 5° C., or less than or equal to 4° C., or less than or equal to 3° C., or less than or equal to 2° C., or less than or equal to 1° C., so that peak positions or peak values of the endothermic peak of the DSC cannot be regarded as absolute.

In the context of the present disclosure, regardless of whether words "approximately" or "about" are used, all numbers disclosed herein are approximate. The value of each number may differ by 1%, 2%, or 5%.

A room temperature refers to a temperature of about 15° C.-32° C. or about 20° C.-30° C. or about 23° C.-28° C. or about 25° C.

The present disclosure also provides a method for preparing a crystal form II of a compound of formula I. The method comprises the following steps:

1. adding any crystal or amorphous (R)-1-(1-(tert-butyloxyl)pyrrolidine-3-yl)-3-cyano-4-(4-(2,6-difluorophenoxyl)phenyl)-1H-pyrrole-2-ethyl formate solid into a solvent, heating and dissolving the solid, and cooling an obtained solution to crystallize; and 2. filtering and drying to obtain a crystal form II of (R)-1-(1-(tert-butyloxyl)pyrrolidine-3-yl)-3-cyano-4-(4-(2, 6-difluorophenoxyl)phenyl)-1H-pyrrole-2-ethyl formate.

In step 1), the solvent is selected from any one or more of the group consisting of alcohol, ketone, nitrile, and ether and ester with no more than four carbon atoms; or a mixed solvent of one or more of the group consisting of alcohol, ketone, nitrile, and ether and ester with water. Preferably, the solvent may be methanol, ethanol, isopropanol, acetone, ethyl acetate, acetonitrile, tetrahydrofuran, ethanol/water, N,N-dimethylformamide/water and 1,4-dioxane/water.

A single solvent or a mixed solvent of the above organic solvents can be used for crystallization.

Further, the single solvent may preferably be ethanol.

A method of recrystallization is not particularly limited and can be performed by a usual recrystallization operation. For example, a raw material compound of formula (I) can be heated and dissolved in an organic solvent, slowly cooled and stirred to crystallize. After the crystallization is completed, it can be filtered and dried to obtain a desired crystal. It should be noted that the filtered crystal is usually vacuum-dried under a reduced pressure and a heating condition of about 30° C.-40° C. to achieve an effect of removing a recrystallization solvent.

Through DSC and XRD pattern measurements, a crystal form of the obtained crystal is studied and a solvent residue of the obtained crystal is detected at the same time.

Studies show that the prepared crystal form II of the compound of formula (I) has significantly better stability than crystal form I under conditions of light and high temperature. The crystal form II has good stability under conditions of grinding and pressure and can meet requirements of production, transportation and storage. A production process is stable, repeatable and controllable, so that the crystal form II can be adapted to industrial production.

DETAILED DESCRIPTION

The present disclosure will be specifically described below with reference to examples. The examples of the present disclosure are provided only to illustrate the technical solutions of the present disclosure, and do not limit the essence and scope of the present disclosure.

Test instruments for experiments
1. DSC pattern
Instrument model: Mettler Toledo DSC 1Staree System
Purge gas: nitrogen
Heating rate: 10.0° C./min
Temperature range: 20° C.-150° C.
2. XRD pattern
Instrument model: Bruker D8Focus X-ray powder diffractometer
Ray: Monochromatic Cu-Kα rays (λ=1.5406)
Scanning method: θ/2θ and scanning range: 2-40°
Voltage: 40 KV and current: 40 mA

Example 1

Figure 1:
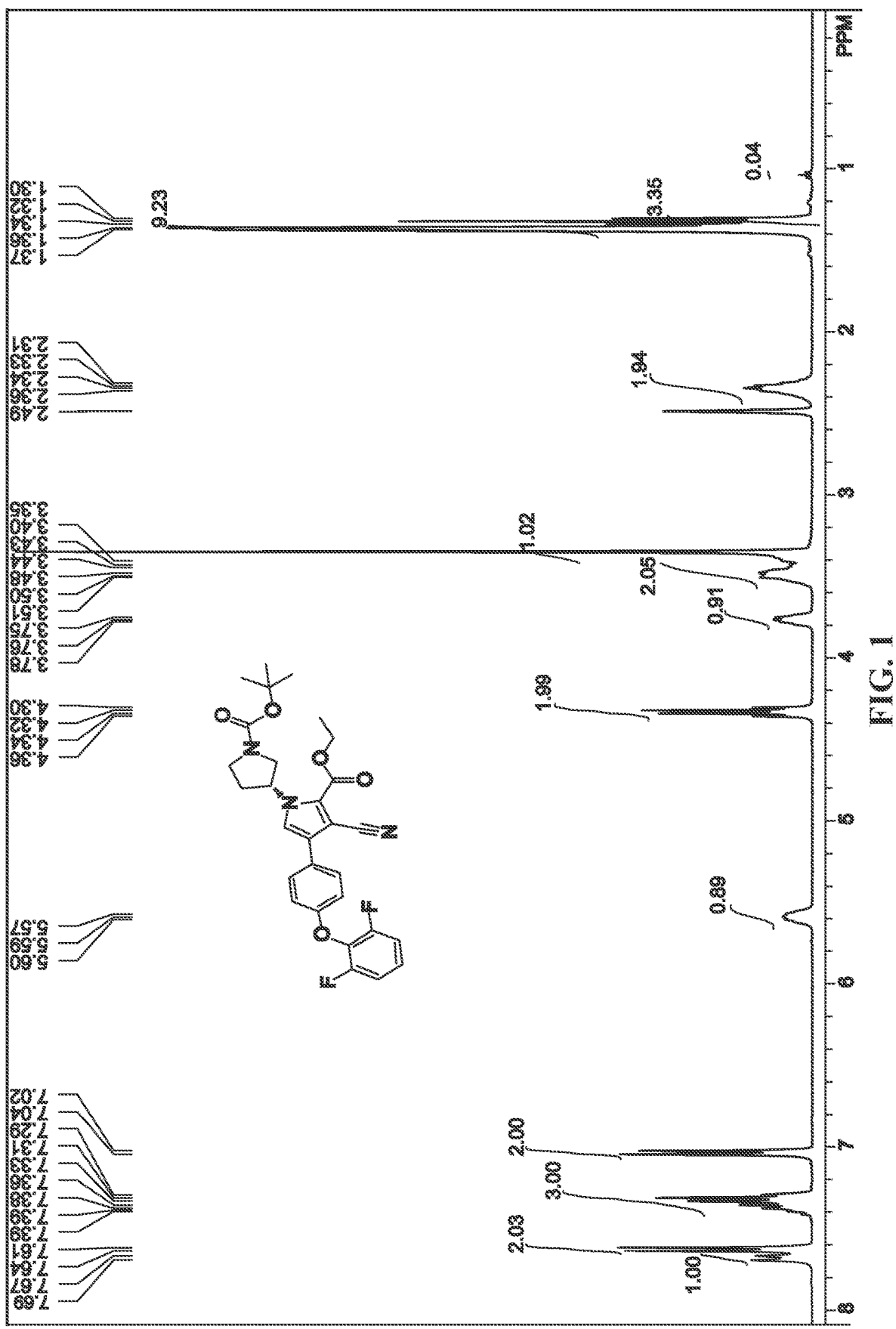
FIG. 1 is an $^1$H Nuclear Magnetic Resonance (HNMR) spectrum of a crystal form I of a compound of formula (I) in Example 1.
Figure 2:
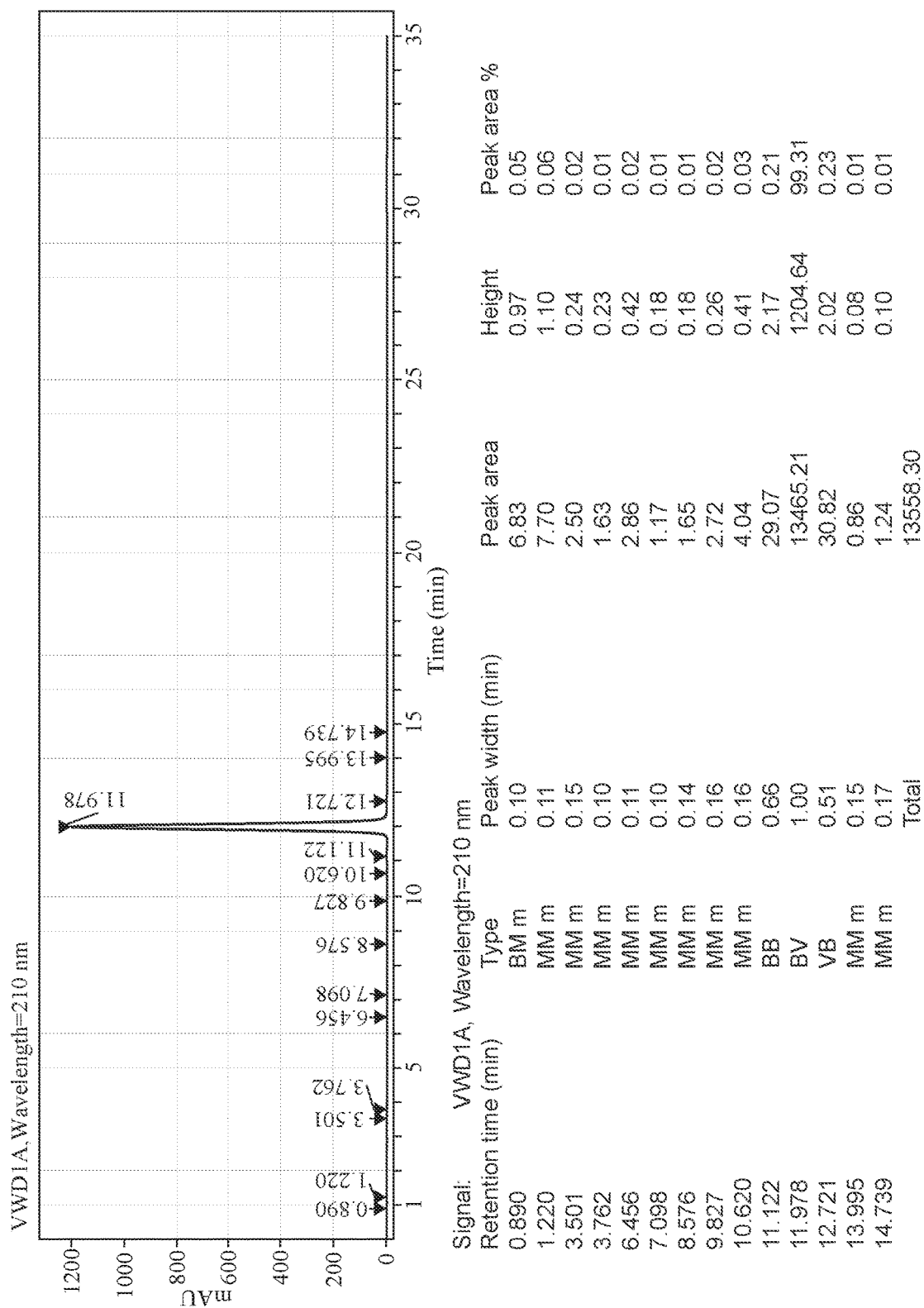
FIG. 2 is a High Performance Liquid Chromatograph (HPLC) diagram of the crystal form I of the compound of formula (I) in Example 1.

Preparation of (R)-1-(1-(tert-butyloxyl)pyrrolidine-3-yl)-3-cyano-4-(4-(2,6-difluorophenoxyl)phenyl)-1H-pyrrole-2-ethyl formate (R)-1-(1-(tert-butoxyyl)pyrrolidine-3-yl)-3-cyano-4-bromo-1H-pyrrole-2-ethy 1 formate (1.98 g, 4.8 mmol), I$_2$ (1.60 g, 4.8 mmol) and K$_3$PO$_4$·3H$_2$O (1.88 g, 7.2 mmol) were dissolved in 1,4-dioxane/water (60 mL/6 mL), an obtained solution was degassed with nitrogen, Pd$_2$(dba)$_3$ (220 mg, 0.24 mmol) and P(Cy)$_3$ (140 mg, 0.48 mmol) were added under nitrogen protection, and a reaction was conducted for 16 h under heating and refluxing. After the reaction, an obtained product was cooled to a room temperature, a solid was filtered out, and a filtrate was concentrated. An obtained residue was purified by a silica gel chromatography (eluent: dichloromethane) and subjected to a rotary evaporation under a reduced pressure to obtain an off-white solid of 0.57 g of (R)-1-(1-(tert-butyloxyl)pyrrolidine-3-yl)-3-cyano-4-(4-(2,6-difluorophenoxyl)phenyl)-1H-pyrrole-2-ethyl formate. HPLC: 99.31% and maximum individual impurity: 0.21%. $^1$H NMR (400 MHz, DMSO-d$_6$): 7.69 (d, 1H), 7.61-7.66 (d, 2H), 7.39-7.29 (m, 3H), 7.02-7.04 (d, 2H), 5.57-5.60 (s, 1H), 4.35-4.30 (dd, 2H), 3.77-3.74 (m, 1H), 3.50-3.44 (m, 2H), 3.40-3.44 (m, 1H), 2.31-2.36 (m, 2H), 1.37-1.36 (s, 9H), 1.33-1.30 (t, 3H). MS(ESI): m/z=538[M+H]$^+$. An X-ray diffraction pattern of the solid sample showed no characteristic absorption peak of a crystal form, as shown in FIG. 1; and a DSC pattern showed a sharp melting endothermic peak at 58.7° C., as shown in FIG. 2, thus the product was determined to be amorphous solid I.

Example 2

Figure 3:
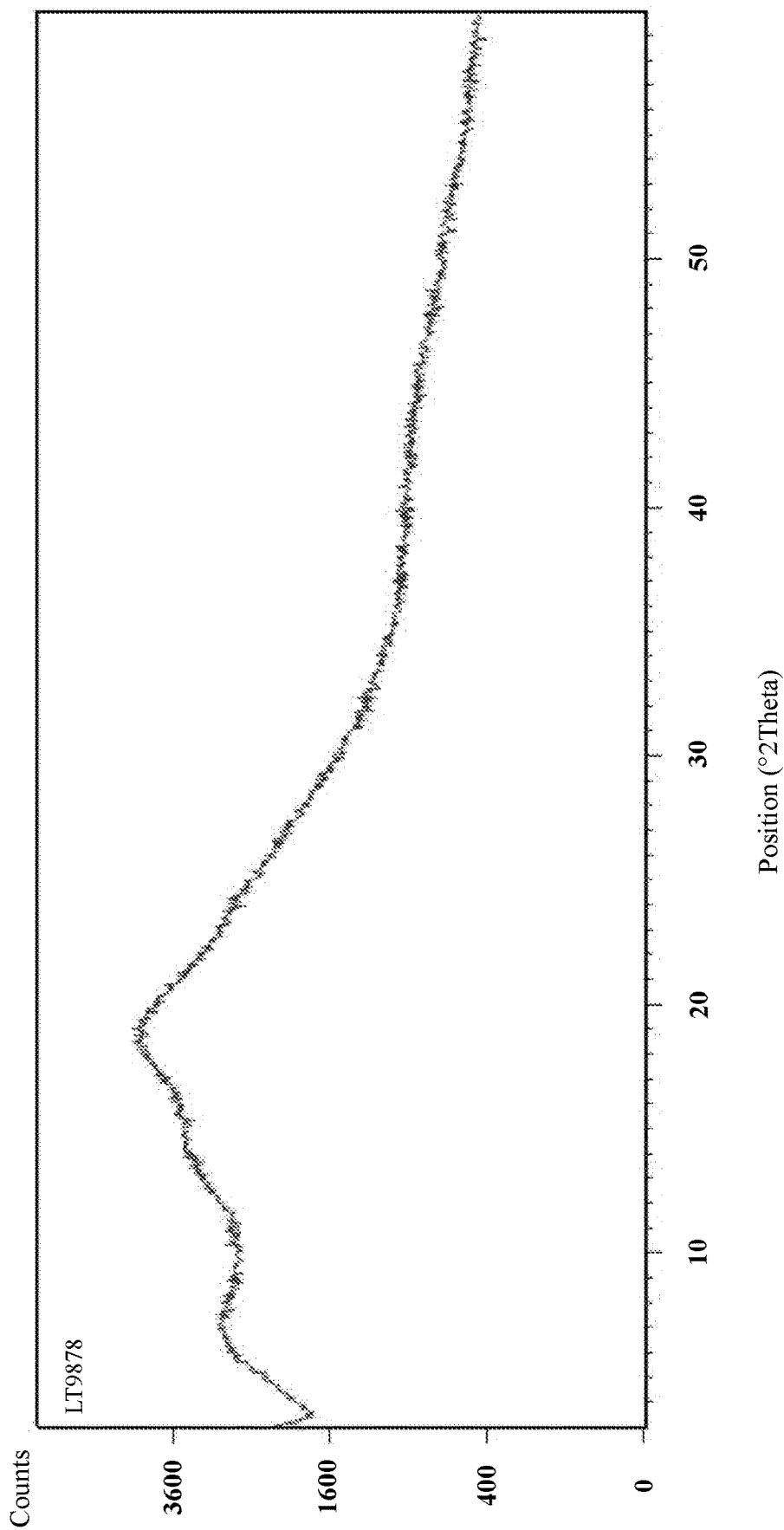
FIG. 3 is an XRD pattern of the crystal form I of the compound of formula (I) in Example 1.
Figure 4:
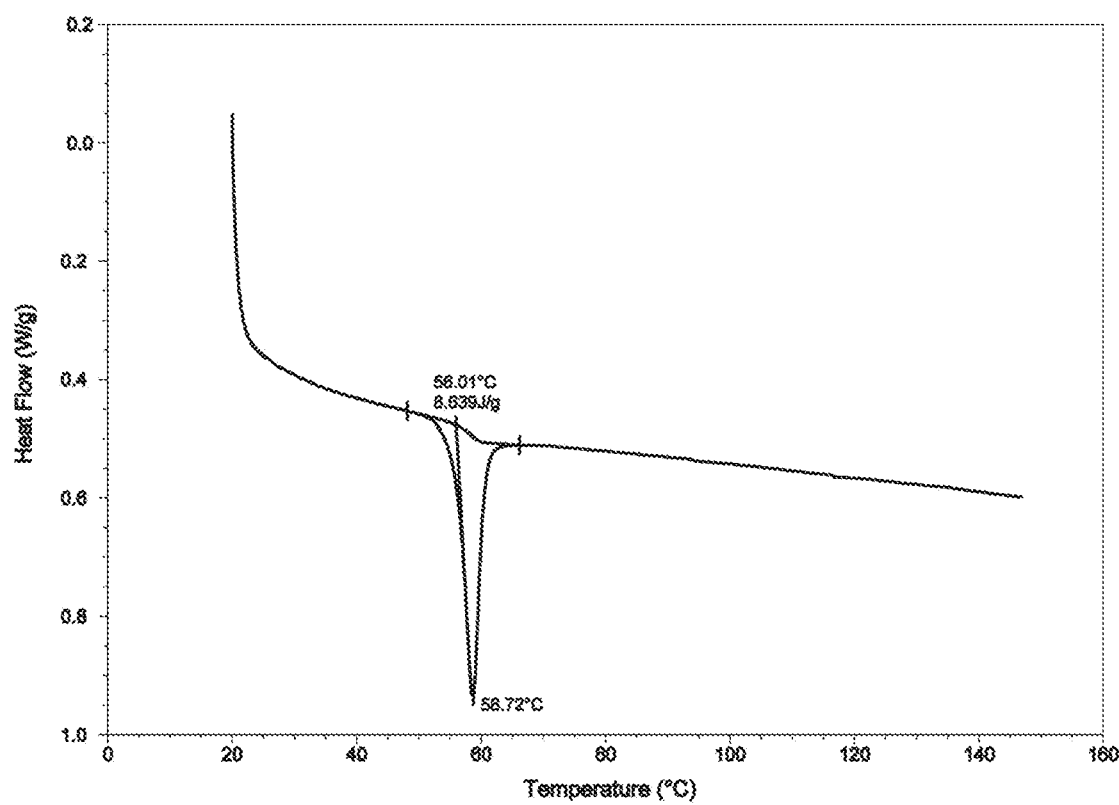
FIG. 4 is a DSC pattern of the crystal form I of the compound of formula (I) in Example 1.
Figure 5:
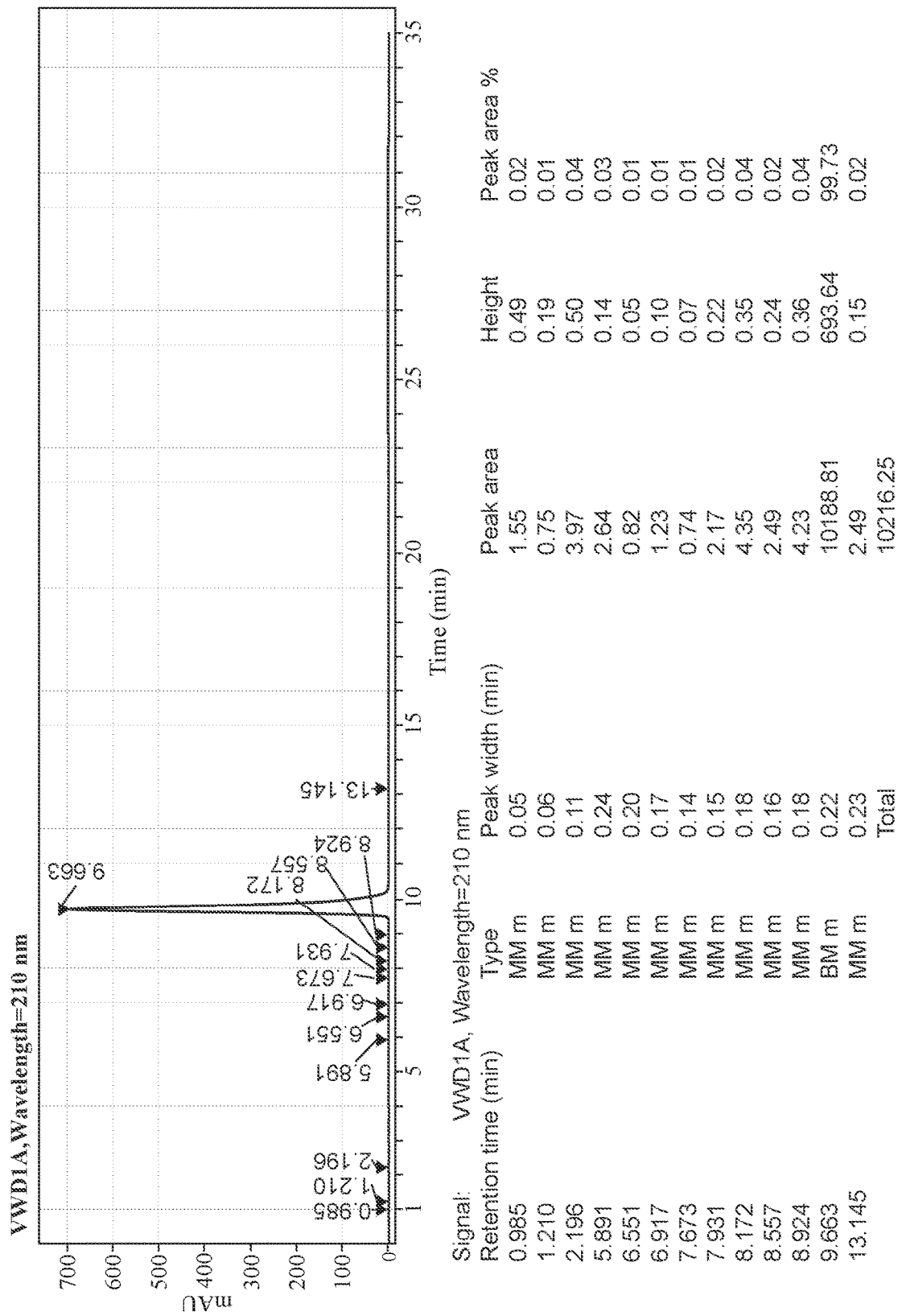
FIG. 5 is an HPLC diagram of a crystal form II of a compound of formula (I) in Example 2.

1.0 g of a compound of formula (I) (a crude product prepared according to Example 1) was taken into a 25-mL single-necked flask, 2 mL of absolute ethanol was added, heating, refluxing and dissolving were conducted, heating was stopped, cooling was conducted for crystallization, suction filtration was conducted the next day, drying was conducted under a reduced pressure, and 715 mg of a white solid was obtained with a yield of 71.5%. HPLC: 99.73% and maximum individual impurity: 0.04%. An X-ray diffraction pattern of the crystal sample was shown in FIG. 3. The X-ray powder diffraction pattern has the following characteristic peaks at 2θ approximately: 5.52, 8.62, 9.34, 11.85, 14.36, 14.52, 15.25, 17.16, 18.79, 19.02, 20.02, 20.18, 20.49, 20.79, 22.44, 23.79, 24.02, 24.29 and 28.18. The positions of the characteristic peaks were shown in Table 1 below. A DSC pattern showed a sharp melting endothermic peak at 97.92° C., as shown in FIG. 4, thus the crystal was defined as a crystal form II. The crystal form II has a content of 97% or more.

TABLE 1

| Characteristic peaks of crystal form II | | | |
|---|---|---|---|
| Peak number | 2θ[°] | d[Å] | I[%] |
| Peak 1 | 5.524 | 15.996 | 26.17 |
| Peak 2 | 8.618 | 10.260 | 13.87 |
| Peak 3 | 9.342 | 9.467 | 71.01 |
| Peak 4 | 11.856 | 7.465 | 30.47 |
| Peak 5 | 14.362 | 6.167 | 100.00 |
| Peak 6 | 14.527 | 6.097 | 46.74 |
| Peak 7 | 15.251 | 5.809 | 31.71 |
| Peak 8 | 15.492 | 5.719 | 9.92 |
| Peak 9 | 17.168 | 5.165 | 51.06 |
| Peak 10 | 18.789 | 4.723 | 65.55 |
| Peak 11 | 19.024 | 4.665 | 73.54 |
| Peak 12 | 20.026 | 4.434 | 16.58 |
| Peak 13 | 20.179 | 4.401 | 22.07 |
| Peak 14 | 20.494 | 4.333 | 33.42 |
| Peak 15 | 20.798 | 4.271 | 33.24 |
| Peak 16 | 21.329 | 4.165 | 13.85 |
| Peak 17 | 21.682 | 4.098 | 15.06 |
| Peak 18 | 22.441 | 3.962 | 46.05 |
| Peak 19 | 23.090 | 3.852 | 11.95 |
| Peak 20 | 23.268 | 3.823 | 11.47 |
| Peak 21 | 23.797 | 3.739 | 24.32 |
| Peak 22 | 24.022 | 3.705 | 31.76 |

TABLE 1-continued

Characteristic peaks of crystal form II

| Peak number | 2θ[°] | d[Å] | I[%] |
|---|---|---|---|
| Peak 23 | 24.292 | 3.664 | 29.48 |
| Peak 24 | 26.933 | 3.310 | 15.70 |
| Peak 25 | 28.183 | 3.166 | 19.10 |
| Peak 26 | 30.135 | 2.965 | 10.07 |

Example 3

1.0 g of a compound of formula (I) (a crude product prepared according to Example 1) was taken into a 25-mL single-necked flask, 1.5 mL of absolute ethanol was added, heating, refluxing and dissolving were conducted, heating was stopped, cooling was conducted for crystallization, suction filtration was conducted the next day, drying was conducted, and 868 mg of a white solid was obtained with a yield of 86.8%. An X-ray diffraction pattern and a DSC pattern of the crystal sample were studied and compared, and the product was determined to be a crystal form II.

Example 4

1.0 g of a compound of formula (I) (a crude product prepared according to Example 1) was taken into a 25-mL single-necked flask, 1 mL of absolute ethanol was added, heating, refluxing and dissolving were conducted, heating was stopped, cooling was conducted for crystallization suction filtration was conducted the next day, drying was conducted, and 934 mg of a white solid was obtained with a yield of 93.4%. An X-ray diffraction pattern and a DSC pattern of the crystal sample were studied and compared, and the product was determined to be a crystal form II.

Example 5

The stability of the crystal forms obtained in Example 1 and Examples 2-4 was compared and the data was shown in Table 2.

TABLE 2

Stability comparison between crystal forms I and II

| Sample | Time (day) | Illumination | 30° C. | 40° C. | RH75% | RH90% |
|---|---|---|---|---|---|---|
| Crystal form I | 0 | 99.31% | 99.31% | 99.31% | 99.31% | 99.31% |
| | 5 | 97.75% | 99.23% | 99.18% | 99.18% | 98.91% |
| | 10 | 95.53% | 99.10% | 99.05% | 98.97% | 98.51% |
| | 30 | 85.76% | 98.87% | 95.01% | 97.41% | 95.91% |
| Crystal form II | 0 | 99.73% | 99.73% | 99.73% | 99.73% | 99.73% |
| | 5 | 99.56% | 99.72% | 99.68% | 99.72% | 99.71% |
| | 10 | 99.43% | 99.72% | 99.65% | 99.68% | 99.61% |
| | 30 | 99.21% | 99.67% | 99.60% | 99.64% | 99.53% |

Stability results showed that when the crystal form I and crystal form II samples were placed under an open condition with light and high temperature, the stability of the crystal form II sample was significantly better than that of the amorphous sample under the conditions of light, high temperature and high humidity.

Example 6

The crystal form II of a compound of formula (I) prepared according to the method of Example 2 was subjected to grinding, heating and tableting. Results showed that the crystal form was stable and detailed experimental data were shown in Table 3 below.

TABLE 3

Research on special stability of crystal form II of a compound formula (I)

| Sample | Treatment | Experimental process | XRD detection | DSC peak value |
|---|---|---|---|---|
| 1 | Grinding for 10 min | A sample 1 of a crystal form II was ground in a mortar for 10 min under nitrogen protection. | Crystal form II | 100.10° C. |
| 2 | Tableting | A sample 2 of a crystal form II was tabletted into tablets | Crystal form II | 101.20° C. |

Experimental Conclusion

Experimental results of influence factors in Table 1 showed that after the crystal form I and crystal form II of the compound of formula (I) were placed for 10 days under conditions of light, temperature at 30° C. and 40° C., high humidity at 75% RH and 90% RH, the purity of the compound was not obviously changed and the compound had good chemical stability; and after the influence factor experiment, the crystal form of the sample was re-tested, and the crystal form was not changed and had stable physical properties.

What is claimed is:

1. A crystal form II of a key intermediate (R)-1-(1-(tert-butyloxyl)pyrrolidine-3-yl)-3-cyano-4-(4-(2,6-difluorophenoxyl)phenyl)-1H-pyrrole-2-ethyl formate of a bruton tyrosine kinase (BTK) inhibitor, wherein an X-ray powder diffraction pattern of the crystal form has the following characteristic peaks at 2θ: 9.34, 11.85, 14.36, 14.52, 15.25, 17.16, 18.79, 19.02, 20.49, 20.79, 22.44 and 24.02 obtained using Cu Kα radiation.

2. The crystal form II according to claim 1, wherein an X-ray powder diffraction pattern of the crystal form has the following characteristic peaks at 2θ: 5.52, 8.62, 9.34, 11.85, 14.36, 14.52, 15.25, 17.16, 18.79, 19.02, 20.02, 20.18, 20.49, 20.79, 22.44, 23.79, 24.02, 24.29 and 28.18 obtained using Cu Kα radiation.

Figure 6:
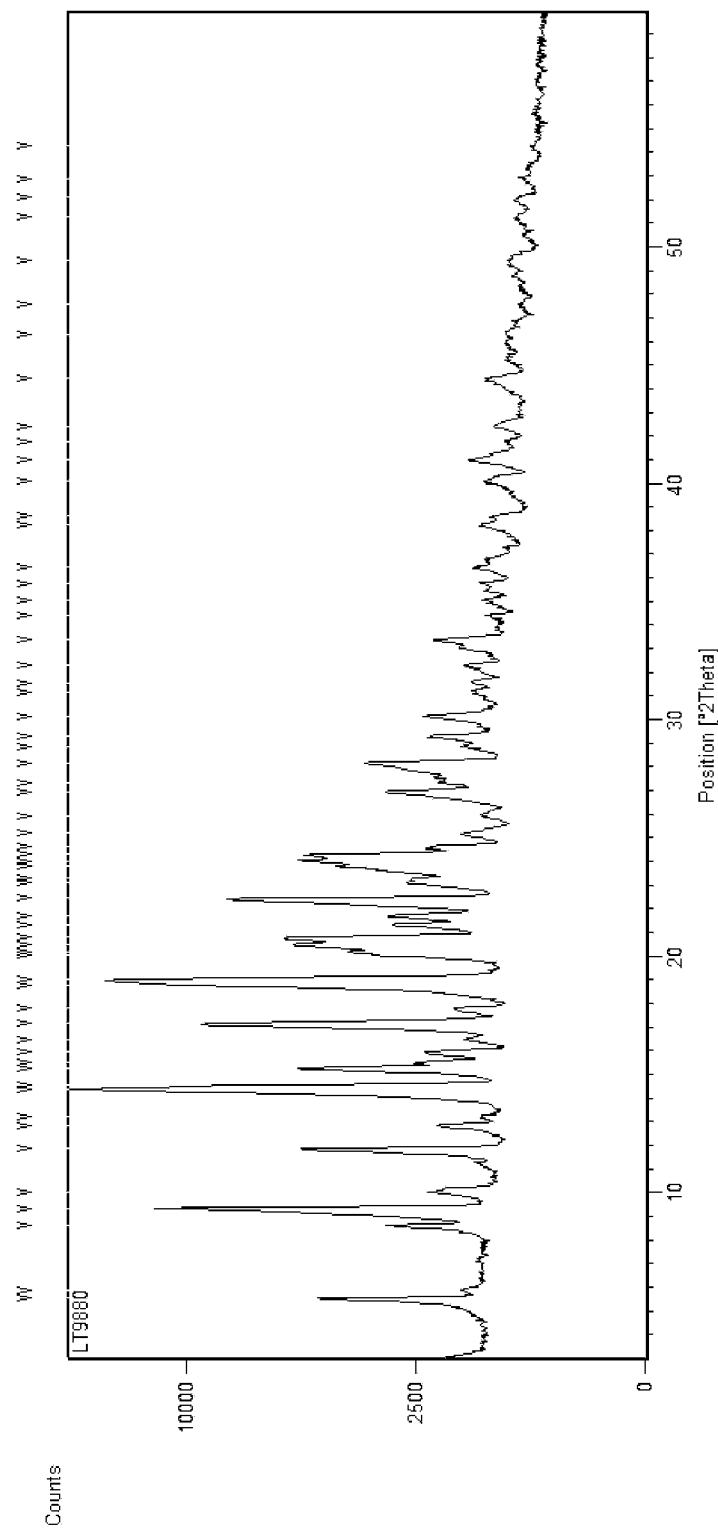
FIG. 6 is an XRD pattern of the crystal form II of the compound of formula (I) in Example 2.
Figure 7:
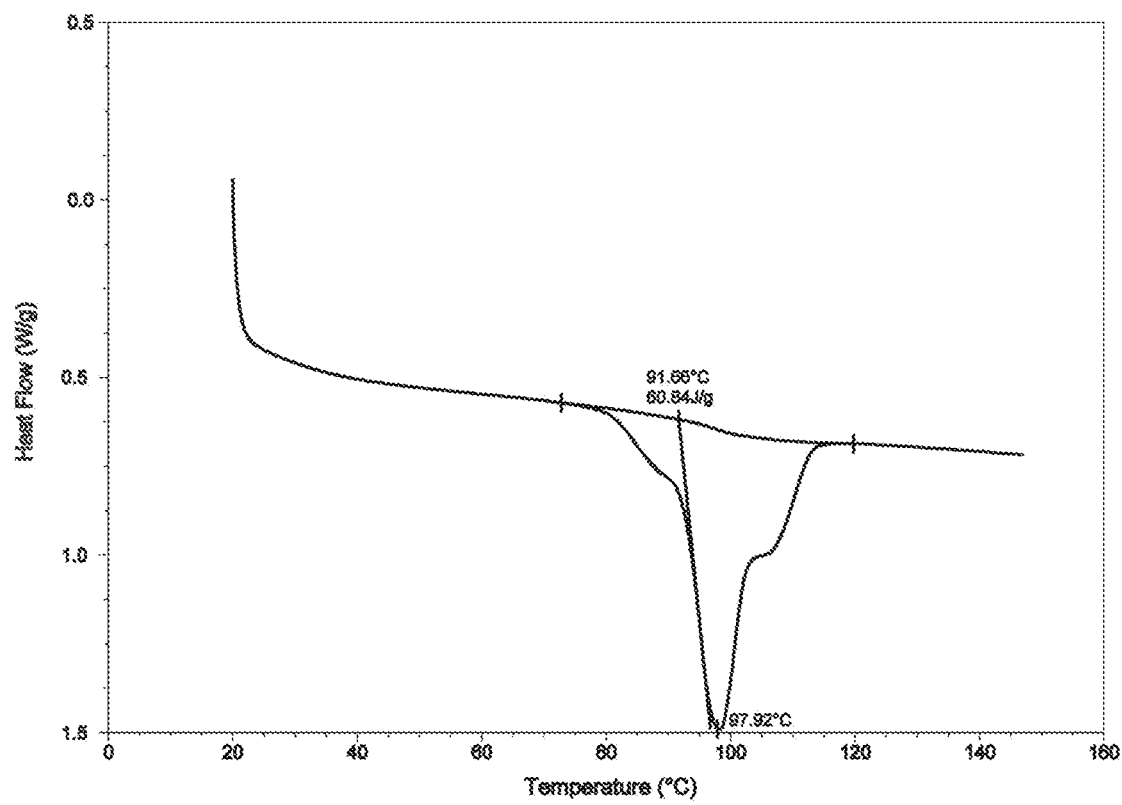
FIG. 7 is a DSC pattern of the crystal form II of the compound of formula (I) in Example 2.

3. The crystal form II according to claim 1, wherein an X-ray powder diffraction pattern of the crystal form is shown in FIG. 6.

4. The crystal form II according to claim 1, wherein a differential scanning calorimetric curve of the crystal form II has an endothermic peak at 95° C.-105° C.

5. The crystal form II according to claim 1, wherein the crystal form II has a content of 97% form II or more.

6. A method for preparing the crystal form II of (R)-1-(1-(tert -butyloxyl)pyrrolidine-3-yl)-3-cyano-4-(4-(2,6-difluorophenoxyl)phenyl)-1H-pyrrole-2-ethyl formate according to claim 1, comprising the following steps: adding any crystal or amorphous (R)-1-(1-(tert-butyloxyl)pyrrolidine-3-yl)-3-cyano-4-(4-(2,6-difluorophenoxyl)phenyl)-1H-pyrrole-2-ethyl formate solid into a solvent, heating and dissolving the solid, cooling an obtained solution to crystallize, and filtering and drying to obtain the crystal form II; wherein the solvent is ethanol.

* * * * *